United States Patent [19]
Keller et al.

[11] Patent Number: 5,190,662
[45] Date of Patent: Mar. 2, 1993

[54] REMOVAL OF IRON SULFIDE PARTICLES FROM ALKANOLAMINE SOLUTIONS

[75] Inventors: Alfred E. Keller, Ponca City; Fred C. Veatch, Newkirk; Arthur L. Cummings; James C. Thompsen, both of Ponca City, all of Okla.; Regina A. Severson, Houston, Tex.

[73] Assignee: Conoco Inc., Ponca City, Okla.

[21] Appl. No.: 737,946

[22] Filed: Jul. 29, 1991

[51] Int. Cl.⁵ .............................................. B01D 15/00
[52] U.S. Cl. ..................................... 210/673; 210/660
[58] Field of Search ............... 210/660, 673, 688, 767, 210/791, 797, 798

[56] References Cited

U.S. PATENT DOCUMENTS

| | | | |
|---|---|---|---|
| 3,732,669 | 5/1973 | Chambers | 55/527 |
| 4,206,049 | 6/1980 | Stana et al. | 210/806 |
| 4,350,590 | 9/1982 | Robinson | 210/492 |
| 4,370,236 | 1/1983 | Ferguson | 210/806 |
| 4,933,071 | 6/1990 | Heyse | 423/139 |

Primary Examiner—Ivars Cintins

[57] ABSTRACT

Aqueous alkanolamine solution containing iron sulfide particles is passed through a bed of contact materials having openings greater than the size of the iron sulfide particles and the iron sulfide particles adhere to the contact material. The contact material is regenerated to sequentially remove alkanolamine and iron sulfide particles by contacting it with water.

9 Claims, 1 Drawing Sheet

REMOVAL OF IRON SULFIDE PARTICLES FROM ALKANOLAMINE SOLUTIONS

BACKGROUND OF THE INVENTION

Alkanolamine sweetening units are used for the removal of $H_2S$ and $CO_2$ from natural gases, enhanced oil recovery gases, refinery hydrodesulfurizer recycle gases, FCCU and Coker gas plant tail gases, LPG streams, and Claus sulfur recovery tail gases. The alkanolamines commonly used are ethanolamine, diethanolamine, methyl diethanolamine, diisopropanol amine, and triethanolamine. These compounds are weak bases in water solution. When solutions of alkanolamines are contacted in packed, sieve plate, bubble cap, or valve tray columns with streams containing $H_2S$ and $CO_2$, the $H_2S$ and $CO_2$ dissolve into the alkanolamine solution The following chemical reactions then take place:

$H_2S + AAmine = AAmineH^+ HS^-$

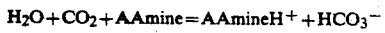

$H_2O + CO_2 + AAmine = AAmineH^+ + HCO_3^-$

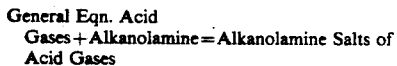

General Eqn. Acid
Gases + Alkanolamine = Alkanolamine Salts of Acid Gases

The solution of water, unreacted alkanolamine, and alkanolamine salts are subjected to steam stripping to decompose the alkanolamine salts and remove $H_2S$ and $CO_2$ from the alkanolamine. The $H_2S$ and $CO_2$ removed from the alkanolamine can then be processed by Claus sulfur recovery, incineration, fertilizer manufacture, or other means.

$H_2S$ and $CO_2$ are not the only gases in the above referred to streams which form weak acids when dissolved in water. Other such acid gases, as they are commonly called, that may appear in gas streams treated with alkanolamine include $SO_2$, COS, or HCN. These gases also undergo the same reactions as $H_2S$ and $CO_2$ to form alkanolamine salts. These salts, though, cannot be removed by steam stripping as $H_2S$ and $CO_2$ salts are. Thus, they remain and accumulate in the system.

Another problem is presented if oxygen gets into the alkanolamine system. Oxidation of acid gas conjugate base anions leads to the formation of other alkanolamine salts, most commonly salts of thiosulfate ($S_2O_3^{-2}$), sulfate ($SO_4^{-2}$) and thiocyanate ($SCN^-$). Other inorganic acid anions such as chloride ($Cl^-$) may also be present. In addition to the inorganic acid anions, the alkanolamine solution may also be contaminated with organic anions such as anions of formic and acetic acid and the like. The alkanolamine salts of these inorganic and organic anions also cannot be regenerated by steam stripping.

Alkanolamine salts which cannot be heat regenerated, called heat-stable salts, reduce the effectiveness of alkanolamine treating. The alkanolamine is protonated and cannot react with either $H_2S$ or $CO_2$ which dissolve into the solution. Also, accumulated alkanolamine salts are known to cause corrosion in carbon steel equipment which is normally used in amine systems. The salts are also known to cause foaming problems which further decrease treating capacity.

The alkanolamine treating process is conducted in metal vessels and lines which are subject to corrosion by the various chemicals passing therethrough. As a result of the corrosion small amounts of iron sulfide are released in the system.

Typically, iron sulfide is removed from the alkanolamine solution by filtration. The filter media has openings which allow the liquid to move through the openings but restrict particles larger than the openings from passing through the openings. Several filter media and filter operations are available. Some filters are single layers of media which stop all particles larger than the opening. They continue to filter by building a cake of the material on the media; the fluid is pushed through the cake by pressure differential, and the particles stick on the top layer of cake. Other filters use fibers as a filter media. The fibers are bound in a three-dimensional structure. As the alkanolamine containing iron sulfide enters the fiber structure, the particles become trapped because the openings between the fibers in the structure are smaller than the particles. The particles remain trapped in the structure increasing the pressure differential through the media.

Both types of filters must be cleaned to remain effective. Both filters are usually cleaned after reaching some predetermined pressure differential caused by buildup of particles in the structure or depth of cake. Single layer (cake filtration) filters can be cleaned by scraping the cake off or backflushing the media to push the cake off. Structured fiber elements are simply replaced with clean ones. The scraped and backflushed filters are reusable.

It would be desirable to provide a process for the removal of iron sulfide particles from alkanolamine solution which is not restricted by pressure drop and in which mechanical cleaning of filter elements is not required.

THE PRIOR ART

U.S. Pat. No. 3,732,669 to Chambers discloses an apparatus for removing solid particles such as iron sulfide from fuel gas by utilizing fiberglass filter cylinders. The filter cylinders are disposed horizontally in a chamber and are spaced from each other. Incoming fuel gas flows downwardly through the filter cylinders and around them. According to the patent, considerable amounts of water and solid materials such as sand, scale and iron sulfide collect on the outer surfaces of the filter cylinders and are then washed downwardly into the space below the bottom row of cylinders. The patent further discloses periodic removal of the filter cylinders for cleaning and/or replacement. The reference is directed to a process in which solid particles are primarily removed by mechanical action, that is by striking the filter media. While some of the particles are retained on the filter media, the majority of the particles are flushed from or fall from the outer surfaces of the cylinders into the bottom portion of the filtering vessel. As stated in the patent, it is necessary periodically to blow out filtered liquid and solid materials from the bottom of the filter in order to reduce pressure drop through the filter.

U.S. Pat. No. 4,933,071 to Hayse discloses a process for the removal of iron from a hydrocarbonaceous feedstock by reacting the iron with sulfur to produce iron sulfide which is then removed by filtration through a fibrous media with glass wool being preferred. Specifically, the patent discloses a process for thermal demetallization in which iron in the hydrocarbonaceous feedstock reacts with sulfur on the fibrous media to form iron sulfide. The process is carried out at temperature between 250° F. and 600° F., and preferably between about 350° F. and 550° F. The material deposited on the fibrous media acts as an active demetallization catalyst and continued thermal desulfurization deposits more of this catalyst on the previously formed catalyst by the process of homoepitaxy. Thus, the system becomes progressively more active for metal removal that is autocatalytic to further iron sulfide formation.

THE INVENTION

According to this invention, aqueous alkanolamine solution containing iron sulfide particles is passed through a contact material having openings greater than the size of the iron sulfide particles, such that flow of alkanolamine solution through the contact material is not impeded, the iron sulfide particles adhere to the contact material and the contact material is regenerated by water washing to remove the iron sulfide particles.

In one aspect of the invention, alkanolamine free of iron sulfide particles is initially removed from the contact material during water washing, followed by removal of iron sulfide particles free from alkanolamine by additional water washing.

DETAILED DESCRIPTION OF THE INVENTION

Figure 1:
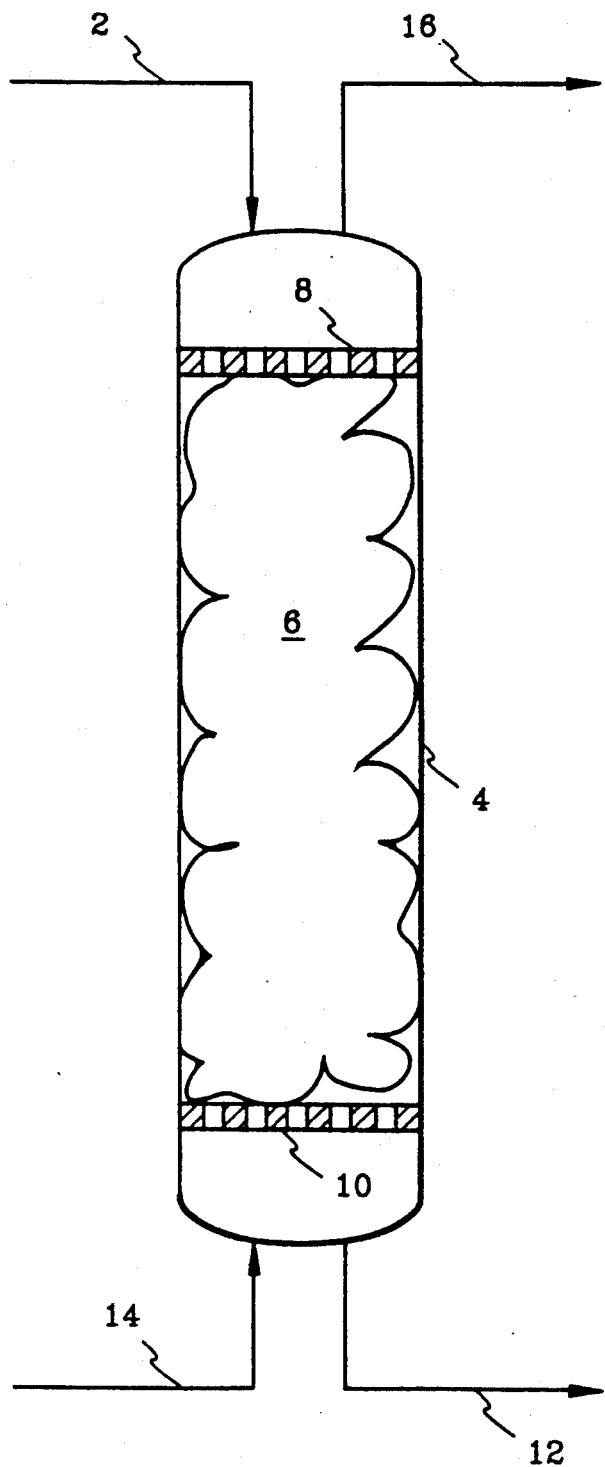
FIG. 1 is a schematic flow diagram including a vessel containing a contact material which illustrates one embodiment of the invention.

The process of the invention may be used to remove iron sulfide particles from any aqueous alkanolamine solution. As previously pointed out, alkanolamine solutions containing iron sulfide particles usually result from processes in which hydrocarbon gases are contacted with an aqueous alkanolamine solution to absorb such impurities as $H_2S$ and $CO_2$. The resulting solutions which contain alkanolamine salts of $H_2S$ and $CO_2$ also contain alkanolamine salts of various inorganic and organic anions which are present in the hydrocarbon gases or are formed in the solution by oxidation resulting from oxygen entering the alkanolamine treating system. The alkanolamine salts of $H_2S$ and $CO_2$ are not heat stable and may readily be decomposed by steam stripping with the concomitant removal of the released $H_2S$ and $CO_2$. The salts of other anions are unaffected by heat or steam stripping so they accumulate in the solution and contribute to corrosion and the accumulation of iron sulfide particles in the alkanolamine solution.

The process of this invention for the removal of iron sulfide particles from an alkanolamine solution is best described by reference to the drawing.

Referring to FIG. 1 an aqueous alkanolamine solution, for example ethanolamine solution, is introduced to a contacting zone 4 through line 2. The contacting zone contains a body of contact material 6, in this instance glass wool, which is confined between two perforated plates 8 and 10. As the ethanolamine solution containing iron sulfide particles passes through the glass wool the iron sulfide in the ethanolamine adheres to the surface of the glass wool. Retention of the iron sulfide is not dependent on any restriction of the size of openings in the glass wool which allow ethanolamine solution and iron sulfide particles to pass through unimpeded. The retention of the iron sulfide on the glass wool is dependent only on the properties of the alkanolamine which surround the iron sulfide particles. Thus, removal of the iron sulfide particles from the ethanolamine is independent of the size of the openings in the glass wool Also, since the iron sulfide particles do not close off openings in the glass wool, the pressure requirements to force ethanolamine solution through the glass wool do not change with accumulation of iron sulfide on the glass wool, as would be the result with conventional filters.

After passing through the glass wool, the aqueous ethanolamine solution now substantially free of iron sulfide is removed from contact zone 4 through line 12 where it may be returned to the gas treating process or subjected to additional processing. After such further processing the alkanolamine solution may be reused in the alkanolamine treating process. Passage of alkanolamine solution through the glass wool is continued until iron sulfide particles break through at which time the glass wool is ready for regeneration.

In the first step of regeneration alkanolamine which remains in the glass wool after the flow of alkanolamine solution is terminated is removed therefrom by passing water through the glass wool co-current to the ethanolamine flow. This may be carried out by introducing water to contact zone 4 through line 2 and removing the water through line 12. In addition to removing free ethanolamine, the water also strips ethanolamine from around the iron sulfide particles. When this occurs, iron sulfide will start to appear in the water wash along with ethanolamine. At this point the ethanolamine which has been removed from the glass wool may be recycled for reuse in the alkanolamine treating process. Additional water is then passed through contacting zone 4 either co-current or countercurrent to the ethanolamine solution with countercurrent flow being preferred. With the ethanolamine removed from the glass wool, the iron sulfide particles no longer adhere to the glass wool and freely move out of contacting zone 4. The effluent water containing iron sulfide particles may be collected and placed in a settling tank, de-watered and drummed for disposal. Alternatively, the iron sulfide may be filtered or centrifuged from the water or it may be acidized with a strong mineral acid, neutralized and discarded to waste water treatment. Upon completion of regeneration the glass wool may be reused for the removal of iron sulfide particles from additional alkanolamine in the same manner as described.

A variety of contact materials may be employed in carrying out the process of the invention. They include but are not limited to such materials as wood, glass, nylon, an aromatic polyamide fiber and other polymers and copolymers.

Glass is the preferred contact material and particularly glass wool, however, any contact material to which iron sulfide particles in alkanolamine solution will adhere may be used in carrying out the process of the invention.

The contact material may be provided in a variety of forms. For example it may be provided in the form of a fine wire-like material as in the case of glass wool. It also may be used in the form of fibers. The contact material is usually present as a relatively dense bed to provide a large surface-to-volume ratio. A large surface-to-volume ratio is preferred in order to minimize the amount of contact material required in the process. The only physical shape requirement of the contact material, however, is that it have sufficient size openings for flow of alkanolamine solution so that there is unobstructed passage of solution through the contact material during the entire iron sulfide removal process. In this manner, flow of alkanolamine solution and iron sulfide particles through the contact material is unimpeded and removal of iron sulfide particles from the alkanolamine solution is provided solely by adherence of these particles to the surface of the contact material.

The volumetric flow rate of the alkanolamine solution through the contact material is dependent on the configuration of the contact material and the cross section of contact material exposed to the alkanolamine solution. Usually the flow rate of alkanolamine solution will vary from between about 0.5 and about 20 gallons per minute per square foot of cross-section. The amount of iron sulfide retained by the contact material is dependent on the surface area of the contact material and the particular contact material used.

The process cycle for the removal of iron sulfide particles from the alkanolamine solution depends on the amount of contact material used, the rate of flow of the alkanolamine solution through the contact material, and the amount of iron sulfide particles contained in the solution. Usually the process may be continued for extended periods, as much as several weeks or more before regeneration of the contact material is required.

The water flow rate used in the regeneration step again is dependent on the amount of contact material and the amount of iron sulfide deposited on the contact material. Usually the water rate will be between about 0.5 and about 20 gallons per minute per square foot of contact material cross-section. Up to several volumes of water per volume of contact material may be required to remove alkanolamine from the contact material prior to breakthrough of the iron sulfide particles during regeneration. Similarly, up to 20 volumes of water per volume of contact material may be used to then remove iron sulfide from the contact material.

The process of the invention has been described in conjunction with a batch operation. The process may also be carried out continuously by providing a plurality of contact zones with appropriate piping and valves.

The invention has been specifically described in its application to the removal of iron sulfide from aqueous ethanolamine, however, any of the other common alkanolamines previously mentioned may be used in the process.

The process of the invention possesses a number of advantages over conventional filtering processes. The contact material is reusable, it does not have to be discarded nor does it have to be cleaned mechanically to remove filter cake. The contacting zone does not have to be opened to remove the contact material since it may be used over and over. The process of the invention is simple in operation. It does not require expensive elements and does not require high pressure washing liquid to remove the iron sulfide from the contact material.

In the conventional filtering process the pressure required to move liquid through the system increases with time as the filtered material builds up in the system, usually in the form of a cake on the filtering medium. Eventually the pressure required becomes so great that it is necessary either to remove and discard the filter or mechanically remove filter cake from the surface of the filter. In the process of the invention, there is never any impedance to flow of the alkanolamine solution through the contact material. While a certain amount of pressure is required to move the alkanolamine solution through the contacting zone, this pressure does not increase significantly with time because of the ability of the alkanolamine solution and iron sulfide particles to move without impedance through the contact material.

The following examples are presented in illustration of the invention.

EXAMPLE 1

Five 250 ml straight wall separatory funnels were packed with the following fibers: wood pulp, glass wool, nylon 66, Kevlar ®, and a copolymer fiber. The fibers were packed down with a glass rod as tight as possible. A layer of inert alumina cylinders were placed on top of the fibers to hold them down. An alkanolamine solution of UCARSOL ® HS-101 a formulated solvent containing methyldiethanolamine (MDEA) at 30 weight percent in water was contaminated with various sized iron sulfide particles washed from a 25 μ paper cartridge filter taken from a commercial amine system. The amine with the iron sulfide particles was placed in separatory funnels above the funnels packed with fibers.

The amine solution was then dripped from each separatory funnel into the funnel with the packed fiber. The filtrate was collected in a beaker below. The solution was filtered until the filtrate began to cloud. Amine flow was then stopped. The amine solution remaining was washed from each fiber with deionized water downflow until no more amine was detected. After rinsing downflow with water, each fiber was washed upflow with deionized water.

All of the packed fibers retained iron sulfide particles from the alkanolamine solution during filtration. The wood pulp, glass wool, and nylon 66 had the highest capacity. The Kevlar ® had less capacity than those three, and the copolymer fibers had the least capacity.

During backflushing, all of the fibers gave up particles of iron sulfide to the water, again varying with the fiber. The wood pulp, Kevlar ®, nylon 66, and glass wool gave up nearly all of the trapped iron sulfide to the backflush water. The copolymer fiber only gave up a small amount of the particles.

This example illustrates that various fibers exhibit the capability for removal of iron sulfide from alkanolamine solution and for backwashing with water to remove the iron sulfide from the packed fibers.

EXAMPLE 2

In this example a 6" diameter 18" long section of sch 40 carbon steel pipe with flanged fittings at the ends was used as the filter housing. Inside the filter housing the following layers from the bottom up were packed: a 1/32" minimum opening stainless steel screen 1/16" thick, 3" of plastic coated aquarium gravel, 10" of packed glass wool, 1" of plastic coated aquarium gravel, 1" of activated carbon, 1" of plastic coated aquarium gravel. The aquarium gravel was approximately ¼ to ½ pieces. The activated carbon layer was added to remove any hydrocarbons from the circulating alkanolamine passing through the filter. Hydrocarbons in the alkanolamine solution adversely affect the iron sulfide removal and backflushing properties of the glass wool.

An unfiltered solution of UCARSOL ® HS-101 containing about 30% MDEA was taken from a commercial alkanolamine system at 130° F. The normal cartridge type filter using 25 micron paper elements was out of service to change the dirty cartridges. The alkanolamine was cooled using a coil submerged in cooling water to about 100° F. The alkanolamine was then pumped through the filter downflow at 3 gal/min for 5 hours. The inlet alkanolamine solution was compared to the outlet solution visually in 10, then 30 minute intervals. After the flow of alkanolamine was stopped, the filter was washed downflow with condensate water cooled to 100° F. The condensate was stopped when no more amine was detected in the outlet. The condensate was switched to upflow and the effluent water was collected in a 55 gal drum. The water was run until no more particulate matter was visible in the effluent. About 10 gal of water was collected. The alkanolamine from the filter was much clearer than the inlet alkanolamine. The removal of the iron sulfide particles in the backflush with condensate was very effective. It produced an opaque, black colored solution which when allowed to settle contained a substantial layer of iron sulfide particles.

EXAMPLE 3

The experiment of Example 2 was repeated with a refinery amine solution with the conventional cartridge filters in service upstream of the experimental filter. Alkanolamine solution passed through the filters at about 3 gpm downflow for a period of five hours. After five hours, samples of the amine solutions entering and leaving the experimental filter were analyzed for total suspended solids (TSS, particles which would not pass through a 0.45 micron filter). Inlet TSS was 10.8 mg/l and outlet TSS was 7.62 mg/1. The glass wool removed solids which were not removed in the cartridge filters.

In all of the examples the flow of alkanolamine containing iron sulfide particles through the various fibers was unimpeded. There was no evidence of any increase in pressure drop through any of the fibers during the tests.

While certain embodiments and details have been shown for the purpose of illustrating the present invention, it will be apparent to those skilled in the art that various changes and modifications may be made herein without departing from the spirit or scope of the invention.

We claim:

1. A process for removing ion sulfide particles from an aqueous alkanolamine solution which comprises passing the alkanolamine solution through a contact material to which iron sulfide particles in an alkanolamine solution adhere, said contact material having openings greater than the size of the iron sulfide particles, whereby flow of alkanolamine solution through the contact material remains unimpeded with no significant increase in pressure drop across the contact material during the process and whereby the iron sulfide particles in the alkanolamine solution adhere to the contact material which does not require periodic removal for cleaning or replacement.

2. The process of claim 1 in which the iron sulfide particles are removed from the contact material by washing the contact material with water.

3. The process of claim 2 in which alkanolamine free of iron sulfide particles is initially removed from the contact material during water washing followed by removal of iron sulfide particles, free of alkanolamine, by water washing the contact material.

4. The process of claim 3 in which the alkanolamine is selected from the group consisting of ethanolamine, diethanolamine, methyldiethanolamine, diisopropanoalmine and triethanolamine.

5. The process of claim 4 in which the contact material is selected from the group consisting of wood, glass, nylon, and an aromatic polyamide fiber.

6. A process for removing iron sulfide particles from an aqueous alkanolamine solution which comprises passing the alkanolamine solution through glass wool having openings greater than the size of the iron sulfide particles, whereby flow of alkanolamine solution through the glass wool remains unimpeded with no significant increase in pressure drop across the contact material during the process and whereby the iron sulfide particles in the alkanolamine solution adhere to the glass wool which does not require periodic removal for cleaning or replacement.

7. The process of claim 6 in which the iron sulfide particles are removed from the glass wool by washing the glass wool with water.

8. The process of claim 7 in which alkanolamine free of iron sulfide particles is initially removed from the glass wool during water washing followed by removal of iron sulfide particles, free from alkanolamine, by water washing the glass wool.

9. The process of claim 8 in which the alkanolamine is selected from the group consisting of ethanolamine, diethanolamine, methyldiethanolamine, diisopropanolamine and triethanolamine.

* * * * *